US008748545B2

(12) United States Patent
Devaux et al.

(10) Patent No.: US 8,748,545 B2
(45) Date of Patent: Jun. 10, 2014

(54) PROCESS FOR PRODUCING BIO-RESOURCED POLYMER-GRADE ACRYLIC ACID FROM GLYCEROL

(75) Inventors: Jean-Francois Devaux, Soucieu En Jarrest (FR); Michel Fauconet, Valmont (FR); Denis Laurent, Saint-Avold (FR)

(73) Assignee: Arkema France, Colombes (FR)

( * ) Notice: Subject to any disclaimer, the term of this patent is extended or adjusted under 35 U.S.C. 154(b) by 533 days.

(21) Appl. No.: 13/119,066

(22) PCT Filed: Sep. 14, 2009

(86) PCT No.: PCT/FR2009/051718
§ 371 (c)(1),
(2), (4) Date: Apr. 6, 2011

(87) PCT Pub. No.: WO2010/031949
PCT Pub. Date: Mar. 25, 2010

(65) Prior Publication Data
US 2012/0108767 A1 May 3, 2012

(30) Foreign Application Priority Data
Sep. 16, 2008 (FR) ...................... 08 56212

(51) Int. Cl.
C07C 57/04 (2006.01)
C07C 51/48 (2006.01)
C07C 51/235 (2006.01)
C08F 20/06 (2006.01)

(52) U.S. Cl.
CPC ................ C08F 20/06 (2013.01); C07C 57/04 (2013.01); C07C 51/48 (2013.01); C07C 51/235 (2013.01)
USPC ....... 526/75; 526/317.1; 526/303.1; 526/328; 562/532; 562/598

(58) Field of Classification Search
CPC ........ C07C 57/04; C07C 51/48; C07C 51/235
USPC ........................................ 526/75, 317.1, 532
See application file for complete search history.

(56) References Cited

U.S. PATENT DOCUMENTS

| 3,689,541 | A |   | 9/1972 | Sennewald et al. |
|---|---|---|---|---|
| 3,701,798 | A |   | 10/1972 | Snapp |
| 3,725,208 | A | * | 4/1973 | Maezawa et al. ................ 203/8 |
| 3,798,264 | A |   | 3/1974 | Kubota et al. |
| 3,932,500 | A |   | 1/1976 | Duembgen et al. |
| 3,933,888 | A |   | 1/1976 | Schlaefer |
| 4,118,588 | A |   | 10/1978 | Fouquet |
| 4,147,718 | A |   | 4/1979 | Gaenzler |
| 5,387,720 | A |   | 2/1995 | Neher et al. |
| 7,179,875 | B2 |   | 2/2007 | Fuchs et al. |
| 7,294,225 | B2 |   | 11/2007 | Landalv |
| 2004/0030046 | A1 |   | 2/2004 | Schultes et al. |
| 2005/0059839 | A1 |   | 3/2005 | Liu |
| 2008/0183013 | A1 |   | 7/2008 | Dubois |
| 2009/0018300 | A1 |   | 1/2009 | Bloom et al. |
| 2009/0068440 | A1 | * | 3/2009 | Bub et al. ................ 428/327 |

FOREIGN PATENT DOCUMENTS

| DE | 10138150 | 2/2003 |
|---|---|---|
| EP | 0270999 | 6/1988 |
| EP | 0286981 | 10/1988 |
| EP | 666831 | 8/1995 |
| EP | 695736 B1 * | 5/1999 |
| EP | 1 061 100 | 6/2000 |
| EP | 1541603 | 6/2005 |
| EP | 1 710 227 | 10/2006 |
| FR | 2119764 | 8/1972 |
| FR | 2223080 | 10/1974 |
| FR | 2347330 | 11/1977 |
| FR | 2377995 | 8/1978 |
| FR | 2400499 | 3/1979 |
| FR | 2446296 | 8/1980 |
| FR | 2554809 | 5/1985 |
| GB | 1491183 | 11/1977 |
| GB | 2001647 | 2/1979 |
| GB | 2 146 636 | 4/1985 |
| JP | 3181440 | 8/1991 |
| WO | 9410085 | 5/1994 |
| WO | 2005095320 | 10/2005 |
| WO | WO 2006/092271 | 9/2006 |
| WO | WO 2006/092272 | 9/2006 |
| WO | 2006114506 | 11/2006 |
| WO | WO 2006/135336 | 12/2006 |
| WO | WO 2006/136336 | 12/2006 |
| WO | 2008067627 | 6/2008 |
| WO | WO 2008/087315 | 7/2008 |
| WO | WO2009/156648 | 12/2009 |

OTHER PUBLICATIONS

Xu X; Lin J; Cen P: "Advances in the Research and Development of Acrylic Acid Production from Biomass"; Chinese Journal of Chemical Engineering, Chemical Industry Press, Beijing, CN; vol. 14, No. 4, 1 aoQT 2006 (Aug. 1, 2006), pp. 419-427, XP022856385.
International Search Report for International Application No. PCT/FR2010/050439, dated Jul. 5, 2010.
International Search Report for International Application No. PCT/FR2009/051718, dated Feb. 15, 2010.
International Search Report for PCT/FR2009/052198 filed Nov. 17, 2009, mailed Jan. 27, 2010.
Spivey, J. J. et al., "Novel Catalysts for the Environmentally Friendly Synthesis of Methyl Methacrylate," Ind. Eng. Chem Res. 1997, 36, 4600-4608.
Ma, X. et al., "Palladium nanoparticles in polyethylene glycols: Efficient and recyclable catalyst system for hydrogenation of olefins," Catalysis Communications 9 (2008) 70-74.

* cited by examiner

Primary Examiner — Yong Chu
(74) Attorney, Agent, or Firm — RatnerPrestia

(57) ABSTRACT

The present invention relates to the manufacture of bioresourced polymer-grade acrylic acid from glycerol. The polymer grade acrylic acid produced has limited content of certain impurities harmful to polymerization processes, such as, total aldehydes, protoanemonin, maleic anhydride and nonphenolic polymerization inhibitors. The invention also relates to the use of the bioresourced acrylic acid obtained for manufacture of superabsorbents or for manufacture of polymers or copolymers using amide or ester derivatives of the bioresourced acrylic acid.

9 Claims, No Drawings

PROCESS FOR PRODUCING BIO-RESOURCED POLYMER-GRADE ACRYLIC ACID FROM GLYCEROL

CROSS-REFERENCE TO RELATED APPLICATIONS

This application is a national stage application under 35 U.S.C. §371 of PCT/FR2009/051718, filed Sep. 14, 2009, which claims benefit to French application FR 0856212, filed on. Sep. 16, 2008, all of which are hereby incorporated by reference.

FIELD OF INVENTION

The present invention is targeted at a process for the manufacture of a bioresourced acrylic acid of polymer grade from glycerol as starting material. The term bioresourced indicates that the acrylic acid is essentially based on a carbon source of natural origin.

BACKROUND OF THE INVENTION

Acrylic acid is a compound which is used essentially, if not virtually solely, as polymerization monomer or comonomer for the manufacture of a very broad range of final products. These final products are manufactured by polymerization of the acid or of the derivatives of this acid, in the ester (polyacrylates) or amide (polyacrylamides) form. A very important outlet for acrylic acid is the manufacture of superabsorbents, in which a partially neutralized (mixture of acrylic acid and sodium acrylate or acrylates of other cations) acrylic acid is polymerized or else acrylic acid is polymerized and the polyacrylic compound obtained is partially neutralized. These polymers are used as is or as copolymers in fields as varied as hygiene, detergents, paints, varnishes, adhesives, paper, textiles, leather, and the like.

Manufacturers have been developing processes for the synthesis of acrylic acid for decades.

The first generation used, as starting material, compounds comprising a triple bond of acetylenic type which were reacted with a mixture of carbon monoxide and water in the presence of a nickel-based catalyst.

The second generation of processes, which is today the most widely employed industrially, makes use of a reaction for the catalytic oxidation of propylene and/or propane using oxygen or an oxygen-comprising mixture.

This reaction is generally carried out in the gas phase and generally in two stages: the first stage carries out the substantially quantitative oxidation of the propylene to give an acrolein-rich mixture, in which acrylic acid is a minor component, and then the second stage carries out the selective oxidation of the acrolein to give acrylic acid.

The reaction conditions of these two stages, carried out in two reactors in series or in a single reactor comprising the two reaction stages in series, are different and require catalysts suited to the reaction; however, it is not necessary to isolate the acrolein from the first stage during this two-stage process.

The starting materials used result from oil or natural gas and consequently the acrylic acid is formed from a nonrenewable fossil carbon starting material. In addition, the processes for extracting, purifying and synthesizing the starting materials and the processes for destroying, at the end of the cycle, the manufactured finished products based on these fossil starting materials generate carbon dioxide, the latter being a direct byproduct of the reactions of the oxidation of propylene to give acrolein and then of acrolein to give acrylic acid. All this contributes to increasing the concentration of greenhouse gases in the atmosphere. In the context of the commitments of the majority of industrialized countries to reduce emissions of greenhouse gases, it appears particularly important to manufacture novel products based on a renewable starting material, contributing to reducing these environmental effects.

For several years, manufacturers have been carrying out research and development studies on "bioresourced" synthetic processes using naturally renewable starting materials. Specifically, in order to limit the ecological impact of conventional production processes, alternative processes starting from nonfossil plant starting materials have recently been developed. Examples are processes using, as starting material, 2-hydroxypropionic acid (lactic acid) obtained by fermentation of glucose or molasses originating from the biomass. Further processes are those starting from glycerol (also known as glycerin), resulting from the methanolysis of vegetable oils at the same time as the methyl esters, which are themselves employed in particular as fuels in gas oil and domestic heating oil. The methanolysis of vegetable oils or animal fats can be carried out according to various well-known processes, in particular by using homogeneous catalysis, such as sodium hydroxide or sodium methoxide in solution in methanol, or by using heterogeneous catalysis. Reference may be made on this subject to the paper by D. Ballerini et al. in l'ActualitéChimique of Nov-Dec 2002.

The processes using hydroxypropionic acid as starting material have a major disadvantage from the economic viewpoint. They involve a fermentation reaction which is necessarily carried out under highly dilute conditions in water. In order to obtain acrylic acid, a very large amount of water has to be removed by distillation, at the price of a very high energy cost. Furthermore, the energy expended to separate the water, which energy is produced from fossil material, will be highly damaging to the initial advantage of producing acrylic acid from this bioresourced starting material. Mention may be made, in this field, of application WO2006/092271, which describes a process for the production of polymers from acrylic acid prepared by the enzymatic route, in particular from carbohydrate.

It has been known for a long time that it is possible, starting from natural organic substances, such as polyols, capable of being converted by a chemical route, to obtain acids or aldehydes comprising 3 carbon atoms per molecule which can constitute precursors of acrylic acid. Mention may be made, by way of example, of the synthesis of acrolein obtained by dehydration of glycerol, which is described in particular in patent U.S. Pat. No. 5,387,720. Glycerol (also known as glycerin) results from the methanolysis of vegetable oils at the same time as the methyl esters, which are themselves employed in particular as fuels in gas oil and domestic heating oil. This is a natural product which enjoys a "green" aura, it is available in large amounts and it can be stored and transported without difficulty. Many studies have been devoted to giving economic value to glycerol according to its degree of purity and the dehydration of glycerol to give acrolein is one of the routes envisaged.

The reaction involved in order to obtain acrolein from glycerol is:

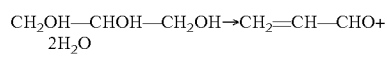

This stage is followed by a stage of conventional oxidation of the acrolein in order to obtain the acrylic acid according to the reaction:

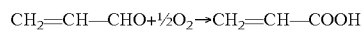

Patent applications EP 1 710 227, WO2006/135336, WO2006/092272 and WO2007/0219521 describe processes for the synthesis of acrylic acid from glycerol comprising the stage of gas-phase dehydration in the presence of catalysts composed of inorganic oxides (which may or may not be mixed) based on aluminum, titanium, zirconium, vanadium, and the like, and the stage of gas-phase oxidation of the acrolein thus synthesized in the presence of catalysts based on oxides of iron, molybdenum, copper, and the like, alone or in combination in the form of mixed oxides.

However, they do not give precise details with regard to the phase of purification of the acrylic acid and do not describe at all what impurities are or are not present in the acrylic acid obtained. For example, application WO2006/092272 describes a process for the manufacture of acrylic acid and of superabsorbent from glycerol. It is asserted therein that it is possible to obtain an acrylic acid with a purity of 99 to 99.98% without specifying how it is obtained and what the residual impurities are. In example 2, it is simply specified that an acrylic acid which does not comprise protoanemonin is obtained without considering the other impurities capable of having an effect on the subsequent polymerizations.

Acrylic acid is intended for the use by manufacturers of processes for the polymerization either of acrylic acid or of its ester derivatives, which processes are carried out under various forms, in bulk, in solution, in suspension or in emulsion. These processes can be highly sensitive to the presence in the charge of certain impurities, such as aldehydes or unsaturated compounds, which can sometimes prevent the expected use value from being obtained, for example by limiting the conversion of the monomer to give the polymer, by limiting the chain length of the polymer or by interfering in the polymerization in the case of unsaturated compounds. Other impurities, such as nonpolymerizable saturated compounds, can be particularly troublesome in the final application by modifying the properties of the finished product, by conferring toxic or corrosive properties on the finished product or by increasing polluting organic discharges during the stages of manufacture of the polymer and/or of the finished product.

Operators are proving to be demanding as regards quality specifications for acrylic acid (or for its ester). The latter must meet strict thresholds as regards impurities. Specifically, users of acrylic acid or of acrylic esters which produce polymers employ formulations suited to the production of their polymers from a "standard" grade of acrylic acid or of esters today manufactured solely from propylene. A modification to the formulations used by these users, for the purpose of adapting them to a different grade of acrylic acid or of esters produced by a route other than that of the conventional processes starting from propylene, would exhibit significant disadvantages for these user companies. Apart from the additional research and development costs, the production of one type of polymer on the same unit starting from different grades of acrylic acid or of esters according to their origin, fossil or bioresourced (such as glycerol), would occasion significant conversion costs and a more complicated production infrastructure.

The need is now making itself felt for the marketing of an acrylic acid which meets all the abovementioned constraints, both upstream, that is to say an acrylic acid essentially based on a nonfossil natural carbon source, and downstream, that is to say an acrylic acid which meets quality standards allowing it to be used in the manufacture of a broad range of technical polymers, without, however, requiring a sophisticated and therefore expensive purification.

The aim of the present invention is to overcome the previous disadvantages by providing a process for the manufacture of a bioresourced acrylic acid of polymer grade, this grade being defined by limiting thresholds for content of the impurities harmful to a broad range of polymerization processes.

SUMMARY OF INVENTION

The subject matter of the invention is a process for the manufacture of a bioresourced acrylic acid of polymer grade having a content by weight of acrylic acid>99% and the following contents of impurities:
total aldehydes<10 ppm
protoanemonin<5 ppm
maleic anhydride<30 ppm
nonphenolic polymerization inhibitors<10 ppm
and a content by weight of $^{14}C$ such that the $^{14}C/^{12}C$ ratio>$0.8\times10^{-12}$.

The acrylic acid obtained by the process of the invention will preferably have a content of
protoanemonin<3 ppm
total aldehydes<3 ppm
maleic anhydride<15 ppm
nonphenolic polymerization inhibitors<3 ppm
and a content by weight of $^{14}C$ such that the $^{14}C/^{12}C$ ratio>$1\times10^{-12}$.

DETAILED DESCRIPTION OF CERTAIN EMBODIMENTS OF THE INVENTION

The invention is targeted at a process for the manufacture of an acrylic acid of polymer grade by using glycerol as starting material, which glycerol will be converted in two stages—dehydration and oxidation—as mentioned above incorporated in an overall purification process.

This process is highly analogous to the synthetic process starting from propylene insofar as the intermediate product, acrolein, resulting from the first stage is the same and insofar as the second stage is carried out under the same operating conditions. However, the reaction of the first stage of the process of the invention, the dehydration reaction, is different from the reaction for the oxidation of propylene of the usual process. The dehydration reaction, performed in the gas phase, is carried out using different solid catalysts from those used for the oxidation of propylene. The acrolein-rich effluent resulting from the first dehydration stage, intended to feed the second stage of oxidation of acrolein to give acrylic acid, comprises a greater amount of water and in addition exhibits substantial differences as regards byproducts resulting from the reaction mechanisms involved given solid form by different selectivities in each of the two routes.

The use of carbon-based starting materials of natural and renewable origin can be detected by virtue of the carbon atoms participating in the composition of the final product. This is because, unlike substances resulting from fossil materials, substances composed of renewable starting materials comprise $^{14}C$. All carbon samples drawn from living organisms (animals or plants) are in fact a mixture of 3 isotopes: $^{12}C$ (representing~98.892%), $^{13}C$ (~1.108%) and $^{14}C$ (traces: $1.2\times10^{-10}$%). The $^{14}C/^{12}C$ ratio of living tissues is identical to that of the atmosphere. In the environment, $^{14}C$ exists in two predominant forms: in inorganic form, that is to say carbon dioxide gas ($CO_2$), and in organic form, that is to say carbon incorporated in organic molecules. In a living organism, the $^{14}C/^{12}C$ ratio is kept constant metabolically as the carbon is continually exchanged with the environment. As the proportion of $^{14}C$ is substantially constant in the atmosphere, it is the same in the organism, as long as it is living, since it absorbs the $^{14}C$ like it absorbs the $^{12}C$. The mean $^{14}C/^{12}C$ ratio is equal to $1.2 \times 10^{-12}$. $^{12}$C is stable, that is to say that the number of $^{12}$C atoms in a given sample is constant over time. $^{14}$C for its part is radioactive and each gram of carbon of a living being comprises sufficient $^{14}$C isotope to give 13.6 disintegrations per minute.

The halflife (or period) $T_{1/2}$, related to the disintegration constant of $^{14}$C, is 5730 years. Due to this period of time, the $^{14}$C content is regarded as constant in practice from the extraction of the plant starting materials to the manufacture of the final product.

The bioresourced acrylic acid of the invention has a content by weight of $^{14}$C such that the $^{14}$C/$^{12}$C ratio is greater than $0.8 \times 10^{-12}$ and preferably greater than $1 \times 10^{-12}$. This bioresourced acrylic acid can even achieve a ratio equal to $1.2 \times 10^{-12}$ in the case where all of the carbon-based components used for its manufacture are of nonfossil or natural origin.

Currently, there exist at least two different techniques for measuring the $^{14}$C content of a sample:
by liquid scintillation spectrometry
by mass spectrometry: the sample is reduced to graphite or to gaseous $CO_2$ and analyzed in a mass spectrometer. This technique uses an accelerator and a mass spectrometer to separate the $^{14}$C ions from the $^{12}$C ions and to thus determine the ratio of the two isotopes.

All these methods for measuring the $^{14}$C content of substances are clearly described in the standards ASTM D 6866 (in particular D6866-06) and in the standards ASTM D 7026 (in particular 7026-04). The measurement method preferably used is the mass spectrometry described in the standard ASTM D 6866-06 (accelerator mass spectroscopy).

The subject matter of the invention is a process for the manufacture of bioresourced acrylic acid of polymer grade from glycerol, which comprises the following stages:
i) dehydration of the glycerol to give acrolein,
ii) oxidation of the acrolein formed to give acrylic acid,
iii) extraction of the acrylic acid formed by countercurrentwise absorption in the form of an aqueous acrylic acid solution,
iv) dehydration of the solution in the presence of a solvent which is immiscible with water but capable of forming an azeotrope with water,
v) removal of the light compounds, in particular acetic acid and formic acid, by distillation,
vi) removal of the heavy impurities by distillation, in order to obtain an acrylic acid of "technical" grade,
vii) purification by distillation of the technical acrylic acid, in order to obtain an acrylic acid of "polymer" grade, after addition to the acrylic acid of an amino compound which reacts with the aldehydes still present.

Glycerol is a chemical, 1,2,3-propanetriol, which can be obtained either by chemical synthesis, starting with propylene, or as coproduct formed during the methanolysis of vegetable oils or animal fats. The methanolysis of vegetable oils, which constitutes a preliminary stage of the process in the case of integration of the entire oil/fat→acrylic acid line, results, on the one hand, in methyl esters and, on the other hand, in glycerol. The methyl esters are employed in particular as fuels in gas oil and domestic heating oil. With the development of fuels having renewable origins, in particular vegetable oil methyl esters (VOMEs), the production of glycerol according to this production route has greatly increased, the glycerol representing of the order of 10% of the weight of the oil converted.

The glycerin, the name of glycerol when it is in aqueous solution, obtained from vegetable oils or animal fats can comprise salts (NaCl, $Na_2SO_4$, KCl, $K_2SO_4$, and the like). In this case, a preliminary stage of removal of the salts, for example by distillation, by use of ion-exchange resins or by use of a fluidized bed, such as described in French application FR 2 913 974, will generally be present. Mention will in particular be made, among the methods used or studied for the purification and the evaporation of glycerol, of those which are described by G. B. D'Souza in J. Am. Oil Chemists' Soc., November 1979 (Vol 56) 812A, by Steinberner U et al. in Fat. Sci. Technol. (1987), 89 Jahrgang No. 8, pp 297-303, and by Anderson D. D. et al. in Soaps and Detergents: A Theoretical and Practical Review, Miami Beach, Fla., Oct 12-14 1994, chapter 6, pp 172-206. Ed: L Spitz, AOCS Press, Champaign.

Use is generally made of aqueous glycerol solutions having a concentration which can vary within wide limits, for example from 20 to 99% by weight of glycerol; preferably, use is made of solutions comprising from 30 to 80% by weight of glycerol.

The principle of the process for obtaining acrylic acid from glycerol is based on the 2 consecutive dehydration and oxidation reactions:

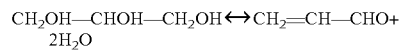

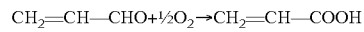

The process can be carried out in two separate stages with two different catalysts.

The dehydration reaction, which is an equilibrium reaction but one promoted by a high temperature level, is generally carried out in the gas phase in the reactor in the presence of a catalyst at a temperature ranging from 150° C. to 500° C., preferably between 250° C. and 350° C., and a pressure between 1 and 5 bar. It can also be carried out in the liquid phase. It can also be carried out in the presence of oxygen or of an oxygen-comprising gas, as described in applications WO 06/087083 and WO 06/114506.

The oxidation reaction is carried out in the presence of molecular oxygen or of a mixture comprising molecular oxygen, at a temperature ranging from 200° C. to 350° C., preferably from 250° C. to 320° C., and under a pressure ranging from 1 to 5 bar, in the presence of an oxidation catalyst.

The glycerol dehydration reaction is generally carried out over solid acid catalysts. The catalysts which are suitable are homogeneous or multiphase substances which are insoluble in the reaction medium and which have a Hammett acidity, denoted $H_0$, of less than +2. As indicated in patent U.S. Pat. No. 5,387,720, which refers to the paper by K. Tanabe et al. in "Studies in Surface Science and Catalysis", Vol. 51, 1989, chap. 1 and 2, the Hammett acidity is determined by amine titration using indicators or by adsorption of a base in the gas phase.

These catalysts can be chosen from natural or synthetic siliceous substances or acidic zeolites; inorganic supports, such as oxides, covered with mono-, di-, tri- or polyacidic inorganic acids; oxides or mixed oxides or heteropolyacids or heteropolyacid salts.

These catalysts can generally be composed of a heteropolyacid salt in which the protons of said heteropolyacid are exchanged with at least one cation chosen from elements belonging to Groups I to XVI of the Periodic Table of the Elements, these heteropolyacid salts comprising at least one element chosen from the group consisting of W, Mo and V.

Mention may particularly be made, among mixed oxides, of those based on iron and on phosphorus and of those based on cesium, phosphorus and tungsten.

The catalysts are chosen in particular from zeolites, Nation® composites (based on sulfonic acid of fluoropolymers), chlorinated aluminas, phosphotungstic and/or silicotungstic acids and acid salts, and various solids of the type comprising metal oxides, such as tantalum oxide $Ta_2O_5$, niobium oxide $Nb_2O_5$, alumina $Al_2O_3$, titanium oxide $TiO_2$, zirconia $ZrO_2$, tin oxide $SnO_2$, silica $SiO_2$ or silicoaluminate $SiO_2/Al_2O_3$, impregnated with acid functional groups, such as borate $BO_3$, sulfate $SO_4$, tungstate $WO_3$, phosphate $PO_4$, silicate $SiO_2$ or molybdate $MoO_3$' functional groups, or a mixture of these compounds.

The preceding catalysts can additionally comprise a promoter, such as Au, Ag, Cu, Pt, Rh, Pd, Ru, Sm, Ce, Yt, Sc, La, Zn, Mg, Fe, Co, Ni or montmorillonite.

The preferred catalysts are phosphated zirconias, tungstated zirconias, silica zirconias, titanium or tin oxides impregnated with tungstate or phosphotungstate, phosphated aluminas or silicas, heteropolyacids or heteropolyacid salts, iron phosphates and iron phosphates comprising a promoter.

Use is made, as oxidating catalyst, of any type of catalyst well known to a person skilled in the art for this reaction. Use is generally made of solids comprising at least one element chosen from the list Mo, V, W, Re, Cr, Mn, Fe, Co, Ni, Cu, Zn, Sn, Te, Sb, Bi, Pt, Pd, Ru and Rh, present in the metallic form or in the oxide, sulfate or phosphate form. Use is made in particular of the formulations comprising Mo and/or V and/or W and/or Cu and/or Sb and/or Fe as main constituents.

When the process is carried out in two stages with two different reactors, it can be advantageous to carry out, between the two reactors, an intermediate condensation of the water, as described in application WO 08/087315.

The conversion of the glycerol to give acrylic acid, which is based on the 2 abovementioned consecutive dehydration and oxidation reactions, can also be carried out in one and the same reactor. In this reaction scheme, known as oxydehydration, the exothermic nature of the oxidation reaction is compensated for by the endothermic nature of the dehydration reaction, which contributes to a better thermal balance of the process. In processes of this type, it is possible either to use two different catalytic beds, an upstream dehydration bed and a downstream oxidation bed, each with their specific catalyst, or a single bed with a "mixed" catalyst composed of a mixture of the dehydration and oxidation catalysts. This version of the process comprising a single reactor involves a recycling (after separation) of the unconverted acrolein in order to carry out the oxidation phase.

The gas mixture resulting from the $2^{nd}$ stage (oxidation reaction) is composed, apart from acrylic acid:
of light compounds which are noncondensable under the temperature and pressure conditions normally employed: nitrogen, unconverted oxygen, carbon monoxide and carbon dioxide, which are formed in a small amount by final oxidation or going round in circles, by recycling, in the process,
of condensable light compounds: in particular water, generated by the dehydration reaction or present as diluent, unconverted acrolein, light aldehydes, such as formaldehyde and acetaldehyde, formic acid and acetic acid,
of heavy compounds: furfuraldehyde, benzaldehyde, maleic acid, maleic anhydride, benzoic acid, 2-butenoic acid, phenol, protoanemonin, and the like.

The second stage of the manufacture consists in recovering the acrylic acid present in the gaseous effluent resulting from the oxidation reaction in order to convert it into acrylic acid of polymer grade of the invention.

The first stage of this purification stage (stage iii of the process according to the invention) consists of an extraction of the acrylic acid by countercurrentwise absorption. For this, the gas resulting from the reactor is introduced at the bottom of an absorption column where it encounters, countercurrentwise, a solvent introduced at the column top. The light compounds, under the temperature and pressure conditions normally employed (respectively more than 50° C. and less than $2\times10^5$ Pa), are removed at the top of this absorption column. The solvent employed in this column is water. The water used as absorbing solvent can be introduced via a source external to the process but will preferably be composed, in all or in part, of water produced during the dehydration stage and condensed by cooling the gaseous reaction stream.

The operating conditions for this absorption stage are as follows:

The gaseous reaction mixture is introduced at the column bottom at a temperature of between 130° C. and 250° C. The water is introduced at the column top at a temperature of between 10° C. and 60° C. The respective amounts of water and of gaseous reaction mixture are such that the water/acrylic acid ratio by weight is between 1/1 and 1/4. The operation is carried out at atmospheric pressure.

In an alternative form of the process, this absorption column can be coupled with a column for the distillation of the very light compounds, essentially acrolein unconverted on conclusion of the reaction, present at a low concentration in the aqueous acrylic acid solution recovered at the bottom of the absorption column. This distillation column, which operates under a pressure of from $6\times10^3$ to $7\times10^4$ Pa, is fed at the top with the bottom stream from the preceding absorption column and makes it possible to remove, at the top, a stream of acrylic acid enriched in acrolein which is recycled in the lower part of the absorption column for final removal at the top of this same column. An aqueous mixture of acrylic acid in water (ratio by weight from 1/1 to 4/1) is thus obtained which is freed from the bulk of the unconverted acrolein, which aqueous mixture is known as "crude acrylic acid".

The second stage of this purification phase (stage iv) is a dehydration stage which is carried out in the presence of a solvent for acrylic acid which is immiscible in water but capable of forming an azeotrope with water.

This solvent will, for example, be chosen from the following solvents: methyl isobutyl ketone (MIBK), trimethylcyclohexanone, butyl acetate, isobutyl acetate, ethyl acetate, ethyl butanoate, heptane, naphthalene, diisobutylene, ethyl methacrylate, propyl acrylate, propyl methacrylate, toluene, toluene+$C_4$-$C_8$ alcohols mixture, mixture of a solvent 1 (propyl acetate or ethyl acetate or ethyl methacrylate or propyl acrylate or propyl propionate)+a solvent 2 ($C_4$-$C_8$ alcohol), mixture of a solvent 1 ($C_7$ hydrocarbon or toluene)+a solvent 2 (ester: ethyl acetate, methyl acrylate, propyl acrylate or ethyl acrylate, or nitrite: acetonitrile or acrylonitrile), mixture of a solvent 1 (diethyl ketone or methyl propyl ketone or MIBK or propyl acetate) +a solvent 2 (toluene, heptane or methylcyclohexane), and the like.

In a first embodiment, this dehydration stage can be carried out by a liquid/liquid extraction of the acrylic acid in the presence of a solvent, followed by a stage of separation of the monomer, acrylic acid, by distillation of the organic phase.

This dehydration phase is described in numerous patents; see, for example, patent FR 2 119 764, with methyl isobutyl ketone (MIBK) as solvent, or patent U.S. Pat. No. 3,689,541, with trimethylcyclohexanone as solvent, or by distillation in the presence of a solvent or of a mixture of solvents forming a heterogeneous azeotrope with water, such as acetates or methyl isobutyl ketone, such as described, for example, in FR 2 554 809, or solvents additionally forming an azeotropic mixture with acetic acid, such as toluene, as described, for example, in JP 03 181 440.

In a second embodiment, use will be made, in the process of the invention preferably for this dehydration stage, of an azeotropic distillation of the aqueous acrylic acid solution using one of the abovementioned solvents and in particular in the presence of a solvent such as MIBK. The distillation column, which operates under a pressure of from $6 \times 10^3$ to $7 \times 10^4$ Pa, is equipped with a decanter which receives the column top stream after condensation and provides for the separation of an upper organic phase, essentially composed of the solvent, which is completely recycled as column top reflux, and of an aqueous phase comprising the water and most of the formaldehyde. The heating power set for the boiler of the column is adjusted so as to obtain a solvent reflux flow rate such that the ratio by weight of solvent returned as reflux to water present in the crude acrylic acid feeding the column corresponds to the theoretical azeotropic mixture (for example: 3/1 in the case of the solvent MIBK). The stream obtained at the column bottom, the dehydrated acrylic acid, is essentially devoid of water (generally less than 1% by weight).

In this alternative embodiment, this column can be coupled to a second column for recovery of the solvent, so as to recover, in the aqueous stream separated by settling at the top of the azeotropic distillation column, the traces of solvent dissolved in the aqueous phase. These small amounts of solvent, distilled and condensed at the top of this solvent recovery column, which operates under atmospheric pressure, are subsequently recycled in the decanter of the preceding column. The aqueous stream from the bottom of this solvent recovery column is discarded.

The third stage of this purification phase (stage v) is a stage of removal of the light compounds, in particular acetic acid and formic acid, by distillation; it is generally known as "topping". The stream of dehydrated acrylic acid obtained at the bottom of the azeotropic distillation column is conveyed to the middle part of a distillation column which operates under a top pressure of the order of $2 \times 10^3$ to $2 \times 10^4$ Pa. The stream from the column bottom comprises acrylic acid freed from the bulk of the light compounds. The column top stream, which is rich in acetic acid and formic acid, can optionally be additionally treated in order to recover, in a second column in series, the small amounts of acrylic acid entrained with the column top stream.

The fourth stage of this purification phase (stage vi) is a stage of separation of the heavy compounds by distillation. The bottom stream from the preceding topping column is introduced at the bottom of a distillation column operating under a top pressure of the order of $2 \times 10^3$ to $2 \times 10^4$ Pa. A stream of purified acrylic acid of technical grade is obtained at the top.

The fifth stage of this purification phase (stage vii) consists in finally purifying the acrylic acid of technical grade to give a polymer grade of acrylic acid. In order to achieve this grade of acrylic acid, which makes it possible to synthesize polymers of high molecular weight, it is particularly important to remove certain aldehydes, such as furfuraldehyde, benzaldehyde and acrolein, down to extremely low contents, which cannot be achieved economically by a simple distillation due to their volatility, which is too close to that of acrylic acid. In order to do this, the aldehydes can be removed by a chemical treatment using a reactant which forms, with these aldehydes, heavy reaction products which can be more easily separated from the acrylic acid by distillation. Use may be made, among the reactants which can be employed, of amines, as described in patent U.S. Pat. No. 3,725,208, and more particularly of the compounds of the family of the hydrazines, such as glycine, as described in patent JP 7.500.014, or hydrazine hydrate, as described in patents U.S. Pat. No. 3,725,208 or JP 7.430.312, or aminoguanidine, as described in patent EP 270 999. These compounds can be used as is or in the form of their salts. The chemical treatments which are described all exhibit the disadvantage of generating water during the reaction of the aldehyde with the amino reactant. The presence of this impurity in the acrylic acid can also be harmful to the manufacture of certain polymers. For this reason, it can be advantageous to carry out this chemical treatment operation during a distillation stage targeted at removing the water and the light compounds at the top, before a stage of distillation of the acrylic acid intended to separate the heavy compounds, as is described in patent JP 7.495.920.

In a preferred embodiment of the process of the invention, the stream of technical acrylic acid is conveyed as feed of a distillation column operating under a top pressure of the order of $2 \times 10^3$ to $2 \times 10^4$ Pa, as a mixture with the amino reactant for removal of the aldehydes chosen from hydrazine derivatives, preferably hydrazine hydrate, introduced in a molar ratio of 2 to 10 with respect to the aldehydes present in the technical acrylic acid. The column top stream, composed essentially of acrylic acid, of water and of acetic acid in a low concentration, can be recycled upstream of the process, for example in the crude acrylic acid stream or as feed of the topping column, in order to recover the acrylic acid. The column bottom stream is, for its part, conveyed to the bottom of a second column operating under a top pressure of the order of $2 \times 10^3$ to $2 \times 10^4$ Pa, in which the heavy compounds are removed at the bottom and the acrylic acid is distilled at the top, in order to obtain a "polymer grade" of acrylic acid.

Acrylic acid is a product which can easily polymerize, in particular during the stages for the purification of the streams rich in this monomer, where the relatively high temperature conditions are favorable to the initiation of the polymerization. As the acrylic acid polymer is insoluble in the monomer, it is essential to introduce polymerization inhibitors into the streams rich in acrylic acid, in all the devices of the purification process.

The polymerization inhibitors generally used for the stages for the purification of acrylic acid are phenolic products, such as hydroquinone or hydroquinone methyl ether, phenothiazine derivatives, compounds of the family of the thiocarbamates, such as copper di(n-butyl)dithiocarbamate, amino derivatives, such as hydroxylamines, hydroxydiphenylamine or derivatives of the family of the phenylenediamines, nitroxide to derivatives of 4-hydroxy 2,2,6,6-tetramethylpiperidine-1-oxyl (TEMPO), such as 4-hydroxy-TEMPO or 4-oxo-TEMPO, or metal salts, such as manganese acetate. These inhibitors can be used alone or in combination and are in addition preferably introduced in combination with an oxygen-comprising gas.

These polymerization inhibitors are generally heavy compounds, the volatility of which is lower than that of acrylic acid. They are removed at the bottom of the columns. On the other hand, their concentration in the vapor phase inside the distillation columns is low and insufficient to prevent the initiation of polymers. In order to prevent the appearance and the accumulation of polymers, these additives are usually introduced into the liquid streams feeding the devices, but also at the top and at various points of the columns and devices, so as to provide continuous and homogeneous reflux of solution rich in polymerization inhibitors over all the parts of the devices. Generally, they are conveyed in solution in a liquid, for example in acrylic acid or in water, if the purification stage relates to aqueous streams.

The acrylic acid of polymer grade obtained at the top of the final distillation column (stage vii) is additivated with hydroquinone methyl ether (HQME), at a concentration of 200

+/−20 ppm; the final product is stabilized by addition of this inhibitor to the column top stream.

The invention also relates to the use of bioresourced acrylic acid of polymer grade in the manufacture of superabsorbents, comprising the polymerization of said partially neutralized acid or the polymerization of said acid, followed by a partial neutralization of the polyacrylic acid obtained.

The invention also relates to the superabsorbents obtained by polymerization of bio-acrylic acid of polymer grade.

The invention is also targeted at the use of bioresourced acrylic acid of polymer grade in the manufacture of polymers or of copolymers by polymerization of the derivatives of said acid in the ester or amide form. It is also targeted at the polymers or copolymers obtained by polymerization of the derivatives, in the ester or amide form, of bioresourced acrylic acid of polymer grade.

The acrylic acid of the invention and its process of manufacture are illustrated in the following examples:

Example 1: preliminary stage of purification of the crude glycerol.
Example 2: conversion of the glycerol to acrolein, followed by condensation of the water.
Example 3: oxidation of acrolein to give acrylic acid.
Example 4: recovery of the crude acrylic acid in the form of an aqueous solution.
Example 5: purification of the crude acrylic acid in order to obtain technical acrylic acid.
Example 6: purification of the technical acrylic acid in order to obtain polymer grade acrylic acid.
Example 7: comparative.

In the examples which follow, the very low concentrations of impurities in the technical acrylic acid and polymer grade acrylic acid streams are measured by the following methods (figures in brackets: accuracy; quantification threshold):

- by high performance liquid chromatography on a Lichrospher 100-RP-18 column, with detection by UV spectrometry and quantification by external calibration: protoanemonin (3%; 0.1 ppm), furfural (1.4%; 0.1 ppm), benzaldehyde (0.2%; 0.25 ppm), maleic anhydride assayed in the form of maleic acid (1.5%; 0.1 ppm); phenothiazine (2%; 0.2 ppm);
- by the same method, with preliminary derivatization in the presence of dinitrophenylhydrazine: formaldehyde (3%; 0.1 ppm);
- by UV/visible spectrometry, after reaction of acrolein with 4-hexylresorcinol in an ethanol/trichloroacetic acid medium catalyzed by mercuric chloride and development of a blue coloration exhibiting a maximum absorbance at 603 nm: acrolein (5%; 0.1 ppm);
- by gas chromatography on an FFAP column, with detection by flame ionization and quantification by internal calibration: acetic acid (3%; 10 ppm).

EXAMPLE 1

The first phase consists in purifying the crude glycerol obtained from the methanolysis of vegetable oils, with removal of the salts. The crude glycerol solution comprises, by weight, 88.5% of glycerol, 5.1% of water and 5.1% of sodium chloride. A stream of 8642 g is continuously conveyed as feed over a 2 liter stirred reactor heated by an external electrical reactor heater. The glycerol and water vapors are condensed in a reflux condenser and recovered in a receiver. This purification operation is carried out under a pressure of 670 Pa. 7695 g of a glycerol solution devoid of sodium chloride are obtained.

EXAMPLE 2

In a second phase, the reaction for the dehydration of the glycerol to give acrolein and the condensation of a portion of the water are carried out. The dehydration reaction is carried out in the gas phase in a fixed bed reactor in the presence of a solid catalyst composed of a tungstated zirconia $ZrO_2/WO_3$ at a temperature of 320° C. at atmospheric pressure. A mixture of glycerol (20% by weight) and water (80% by weight) is conveyed to an evaporator in the presence of air in an $O_2$/glycerol molar ratio of 0.6/1. The gas medium exiting from the evaporator at 290° C. is introduced into the reactor, composed of a tube with a diameter of 30 mm charged with 400 ml of catalyst and immersed in a salt bath ($KNO_3$, $NaNO_3$ and $NaNO_2$ eutectic mixture) maintained at a temperature of 320° C. At the outlet of the reactor, the gaseous reaction mixture is conveyed to the bottom of a condensation column. This column is composed of a lower section filled with Raschig rings surmounted by a condenser in which a cold heat-exchange fluid circulates. The cooling temperature in the exchangers is adjusted so as to obtain, at the column top, a temperature of the vapors of 72° C. at atmospheric pressure. Under these conditions, the loss of acrolein at the condensation column bottom is less than 5%.

EXAMPLE 3

In a third phase, the gas mixture comprising 1.75 mol/h of acrolein is introduced, after addition of air ($O_2$/acrolein molar ratio of 0.8/1) and of nitrogen in an amount necessary in order to obtain an acrolein concentration of 6.5 mol%, as feed of the reactor for the oxidation of acrolein to give acrylic acid. This oxidation reactor is composed of a tube with a diameter of 30 mm charged with 480 ml of catalyst based on Mo/V mixed oxide and immersed in a salt bath, identical to that described in example 2, maintained at a temperature of 250° C. Before introducing over the catalytic bed, the gas mixture is preheated in a tube which is also immersed in the salt bath.

EXAMPLE 4

The fourth phase consists in recovering the acrylic acid present in the gas mixture in the form of an aqueous solution (crude acrylic acid). At the outlet of the second reactor, the gas mixture is introduced at the bottom of a column for counter-currentwise absorption with water operating at atmospheric pressure. This column is filled with random packing of the ProPak type. 110 g/h of water are introduced at ambient temperature at the top of this column. In the lower part, over ⅓ of its total height, the column is equipped with a cooling section which receives, in the bottom part, the reaction gas introduced at 150° C. A portion of the column bottom liquid is withdrawn, cooled through an external exchanger and then recycled at the top of this lower cooling section. The temperature of the vapors at the column top is 75° C. and that of the crude aqueous acrylic acid solution obtained at the column bottom is 80° C. The product obtained at the bottom (crude acrylic acid) comprises, by weight, 50% of acrylic acid, 6.5% of acetic acid and 43% of water.

EXAMPLE 5

The fifth phase consists in purifying the crude acrylic acid in order to obtain the technical acrylic acid grade. In order to do this, use is made of a series of successive distillations. The aqueous solution obtained is subjected first to a distillation in order to remove the water in the form of an azeotropic mixture with methyl isobutyl ketone (MIBK). The column, packed with ProPak elements representing an efficiency of 15 theoretical plates, is fed at its middle with crude acrylic acid and at the top with MIBK in an MIBK/water present in the crude acrylic acid ratio by weight of 3/1. The azeotropic mixture distills at a top temperature of 45° C. under a pressure of $1.2 \times 10^4$ Pa. The dehydrated acrylic acid recovered at the column bottom comprises no more than 1% of water by weight. It is sent as feed of a topping column, which makes it possible to remove the light compounds, essentially acetic acid, at the top. This column, packed with ProPak elements (20 theoretical plates), is fed at its middle with the stream of dehydrated acrylic acid and a stream "rich" in acetic acid is distilled at the top under a pressure of $5.3 \times 10^3$ Pa at a top temperature of 38° C.

The topped acrylic acid recovered at the bottom of this column has a content of acetic acid of 0.1% by weight. It is conveyed as feed of a tailing column provided with 17 perforated plates comprising weirs which makes it possible to remove the heavy compounds at the bottom. This column operates under a pressure of $1.2 \times 10^4$ Pa with a top temperature of 81° C. and with a reflux ratio of 1. The acrylic acid obtained at the column top constitutes the technical acrylic acid (TAA).

The analyses of the technical grade acrylic acid show that the product comprises, by weight, 0.0005% of protoanemonin, 0.0032% of furfural, 0.0005% of benzaldehyde, 0.005% of acrolein, 0.11% of acetic acid and 0.0019% of maleic anhydride.

EXAMPLE 6

The acrylic acid of technical grade is additivated with hydrazine hydrate in a molar ratio of 7/1 with respect to the aldehydes present (furfural, benzaldehyde, acrolein, and the like) and the stream is distilled in a column of 17 perforated plates comprising weirs under a pressure of $9 \times 10^3$ Pa with a top temperature of 69° C.

In all the distillation stages described above, polymerization inhibitors are introduced at the top of the columns, so as to avoid the formation of polymers. The inhibitors used are phenothiazine (PTZ), hydroquinone and hydroquinone methyl ether (HQME) at conventional contents known to a person skilled in the art.

In the final distillation column, phenothiazine is introduced at plate No. 5, counted from the top, and HQME is introduced at the top, in solution in polymer grade acrylic acid. Finally, further HQME is introduced, so as to obtain a concentration of this polymerization inhibitor in the polymer grade acrylic acid of 0.02%.

The analyses of the acrylic acid obtained, of polymer grade, show that the product comprises 1.5 ppm of protoanemonin, 0.8 ppm of furfural, 0.5 ppm of benzaldehyde, 0.2 ppm of acrolein, 4 ppm of acetaldehyde, 0.6 ppm of formaldehyde, 0.15% of acetic acid, 12 ppm of maleic anhydride and 0.2 ppm of PTZ. The product obtained is devoid of hydrazine.

Furthermore, the $^{14}C$ content of the sample, measured according to the standard ASTM D 6866-06, according to the method by mass spectrometry, will be such that the $^{14}C/^{12}C$ ratio will be greater than $0.9 \times 10^{-12}$.

EXAMPLE 7

Comparative

The aqueous acrylic acid solution (crude acrylic acid) obtained in example 4 (540 g) is mixed, as in example 2 of application WO2006/092272, with 50% of its weight of toluene. This mixture is placed, with vigorous stirring, in a jacketed container cooled to 0° C., then stirring is halted and the 2 immiscible phases are allowed to separate by settling for one hour. The toluene-rich organic phase (61.%) is the upper phase. This organic phase (307 g) is separated. It comprises 30% of AA, i.e. only 34.7% of the AA present in the starting mixture. This solution is distilled in a column packed with ProPak elements representing an efficiency of 5 theoretical plates. A first fraction of 226 g, corresponding to the azeotropic mixture rich in toluene and water and distilling at a top temperature of between 31 and 43° C. under a pressure of $9.1 \times 10^3$ Pa, is collected. It comprises 18.6 g of AA (i.e., a loss of 6.9% of the AA present in the starting solution). A second fraction, corresponding to the pure product, distills at a top temperature of 76° C. It has a content of 97.6% of AA and 0.11% of water. This purified product, i.e. 52 g, represents only 19.3% of the AA present in the starting solution, i.e. a recovery yield much too Low for the process to be economically acceptable. In addition, the analysis of this product reveals concentrations by weight of impurities which render it unsuitable for an application for the purpose of the production of polymers: 1.47% of acetic acid, 75 ppm of furfural, 41 ppm of benzaldehyde, 17 ppm of protoanemonin and 8 ppm of maleic anhydride.

What is claimed is:

1. A process for manufacturing polymer grade acrylic acid using naturally renewable starting materials comprising at least the steps of:
   i) dehydrating glycerol to form acrolein;
   ii) oxidizing the acrolein to form acrylic acid;
   iii) extracting the acrylic acid by countercurrentwise absorption and forming an aqueous acrylic acid solution;
   iv) dehydrating the aqueous acrylic acid solution in the presence of at least one solvent to form an acrylic acid mixture, wherein the solvent is immiscible with water and capable of forming an azeotrope with water;
   v) removing one or more light compounds from the acrylic acid mixture by distillation;
   vi) removing one or more heavy impurities from the acrylic acid mixture by distillation to form a technical grade of acrylic acid; and
   vii) purifying by distilling the technical grade of acrylic acid and adding at least one amino compound which reacts with aldehydes in the technical grade acrylic acid to form polymer grade acrylic acid, wherein the polymer grade acrylic acid contains greater than 99% by weight of acrylic acid, less than 5 ppm protoanemonin, less than 10 ppm total aldehydes, less than 30 ppm maleic anhydride, less than 10 ppm nonphenolic polymerization inhibitors, and a content by weight of $^{14}C$ such that the $^{14}C/^{12}C$ ratio is greater than $0.8 \times 10^{-12}$.

2. The process of claim 1, wherein step iii) employs water as an absorption solvent.

3. The process of claim 1, wherein during step iii), the absorption is coupled with a column for distillation of light compounds.

4. The process of claim 1, wherein step iv) is carried out by a liquid/liquid extraction comprising an organic phase, followed by separation of the acrylic acid present in the organic phase by distillation.

5. The process of claim 1 wherein step iv) is carried out by azeotropic distillation.

6. The process of claim 1 wherein step iv), is coupled to a column for recovery of the solvent.

7. The process of claim 1 wherein the solvent in step iv) is methyl isobutyl ketone (MIBK).

8. The process of claim 1, wherein the step vii) purification is carried out using two distillation columns.

9. The process of claim 1 wherein the amino compound is a hydrazine derivative.

* * * * *